United States Patent [19]

Soezima

[11] Patent Number: 4,780,903

[45] Date of Patent: Oct. 25, 1988

[54] X-RAY SOURCE

[75] Inventor: Hiroyoshi Soezima, Kyoto, Japan

[73] Assignee: Shimadzu Corporation, Kyoto, Japan

[21] Appl. No.: 898,998

[22] Filed: Aug. 22, 1986

[30] Foreign Application Priority Data

Aug. 22, 1985 [JP] Japan ................................ 60-185471

[51] Int. Cl.[4] ......................... H01J 35/08; A61N 5/10

[52] U.S. Cl. ..................................... 378/145; 378/119; 378/147

[58] Field of Search ............... 378/119, 145, 147, 149, 378/99, 143

[56] References Cited

U.S. PATENT DOCUMENTS

| | | | |
|---|---|---|---|
| 3,999,096 | 12/1976 | Funk et al. | 378/143 |
| 4,321,473 | 3/1982 | Albert | 378/99 |
| 4,395,775 | 7/1983 | Roberts et al. | 378/145 |
| 4,675,890 | 6/1987 | Plessis et al. | 378/143 |

OTHER PUBLICATIONS

Mosher and Stephanakis, *X-Ray "Light Pipes"*, Applied Physics Letters, vol. 29, No. 2, 15 Jul. 1976, pp. 105-107.

Marton, "*X-Ray Fiber Optics*", Applied Physics Letters, vol. 9, No. 5, 1 Sep. 1966, pp. 194 and 195.

Vetterling and Pound, *Measurements on an X-Ray Light Pipe at* 5.9 & 14.4 *keV*, J. Opt. Soc. Am., vol. 66, No. 10, Oct. 1976, pp. 1048-1049.

*Primary Examiner*—Carolyn E. Fields
*Assistant Examiner*—Joseph A. Hynds
*Attorney, Agent, or Firm*—Birch, Stewart, Kolasch & Birch

[57] ABSTRACT

An X-ray source includes a thin film X-ray target for generating and focusing X-rays in response to the application of electron beams, and a capillary tubular element for allowing the X-rays to pass. The capillary tubular element has such a diameter the beams of the X-rays impinging on the inner surfaces of the capillary tubular element are totally reflected. Additionally, a thin film is provided for adsorbing the electron beams, but allowing the X-rays to penetrate.

5 Claims, 4 Drawing Sheets

X-RAY SOURCE

BACKGROUND OF THE INVENTION

The present invention relates to an X-ray source in general and, more particularly, an X-ray source for generating a small X-ray beam toward a small area of a specimen to be examined, suitable for an X-ray photoelectron spectroscopy (XPS) or an X-ray fluorescence spectroscopy, or an X-ray lithograph.

Conventionally, it is very difficult to focus the diameter of an X-ray beam in the order of, for example, 100 μm or less. Some attempts have been proposed as described below with reference to FIGS. 6–9. In an X-ray source of FIG. 6, an electron beam 2 is emitted toward a target 4, so that part of X-ray beam 6 generated from the target 4 are focused using a spherical spectroscopic crystal 8. In the X-ray source of FIG. 7, part of the X-ray beams 6 generated from the target 4 in response to the irradiation of the electron beam 2 are focused using a cylindrical total reflection surface 10. This surface 10 serves to totally reflect the part of the X-ray beams 6. With reference to the X-ray source of FIG. 8, part of the X-ray beams 6 generated from the target 4 in response to the irradiation of the electron beam 2 are focused with the diffraction phenomenon using Fresnel zone plate 12. Further, with reference to FIG. 9, a specimen 14 is closely binded with a thin film target 16. The electron beam 2 is applied to the thin film target 16 in an attempt to produce the X-ray beams 6 from a small point of the thin film target 16.

In the above-described X-ray sources of FIGS. 6 to 8, only part of the X-ray beams 6 generated from the target 4 are focused with the spherical spectroscopic crystal 8 or the zone plate 12 while the other part of the X-ray beams are astray. Therefore, it is difficult to provide strong X-ray beams of small diameters.

Further, in the X-ray source of FIG. 9, the thin film target 16 and the specimen 14 must be closely found so that this type of X-ray source should be limited to a specific purpose, for example, in which the thin film target 16 is used to be exposed to the electron beam 2, whereby the X-rays 6 are emitted from the opposing side to the thin film target 16.

SUMMARY OF THE INVENTION

Accordingly, it is an object of the present invention to provide an improved X-ray source for generating small and strong X-ray beams toward a fine point of a specimen, suitable for any general purpose.

It is another object of the present invention to provide an improved solid-surface analyzer such as an X-ray photoelectron spectroscopy (XPS) comprising an X-ray source for generating small and strong X-ray beams toward a fine point of a specimen.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, an X-ray source suitable for an X-ray photoelectron spectroscopy (XPS) comprises a plurality of capillary tubular elements and an X-ray target. An electron beam is irradiated to the X-ray target. Each of the plurality of capillary tubular elements has a diameter great enough to totally reflect an X-ray beam emitted from the X-ray target. Preferably, each of them is about 10–20 μm in diameter and about 0.5–1 mm in length. Since the X-ray beam generated from the X-ray target is totally reflected through each of the plurality of capillary tubular elements, the X-ray beam can be focused.

Additionally, a thin film layer may be provided at the outlet of each of the plurality of capillary tubular elements, for allowing the X-ray beam to penetrate and absorb the electron beam.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE PREFERRED EMBODIMENT

Figure 1:
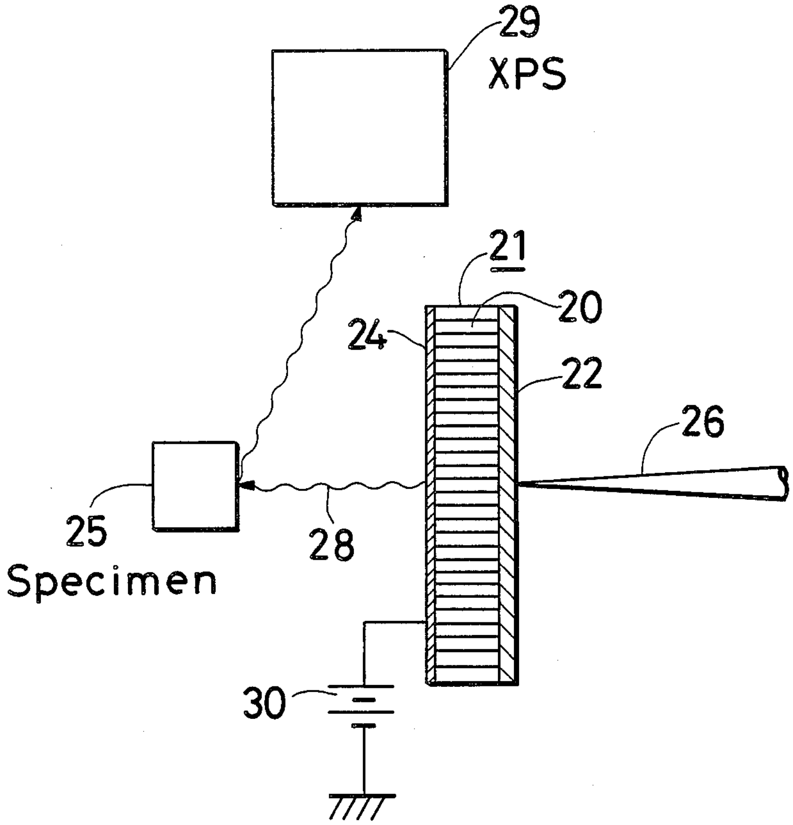
FIG. 1 is a cross-sectional view of an X-ray source according to a preferred embodiment of the present invention.

FIG. 1 is a cross-sectional view of an X-ray source according to a preferred embodiment of the present invention. In the X-ray source, a plurality of capillary tubular elements 20 are bundled so that their edges are aligned to provide a plate 21. Preferably, the diameter of each of the plurality of capillary tubular elements is about 10–20 μm and the length is about 0.5–1.0 mm. The capillary tubular element is made of a molten crystal. The number of the capillary tubular elements bundled is in the order of ten thousand or less about several tens thousand, or one hundred thousand or more, depending on the usage of the X-ray source.

A thin film X-ray target 22 is provided at the side of the plate 21 comprising the plurality of capillary tubular elements 20.

Preferably, the thin film X-ray target 22 may be an aluminum layer of about 5 μm in thickness. It may be possible that it is a thin film of magnesium.

Additionally, a thin film 24 may be provided at the opposing side of the plate 21. The thin film 24 is provided for allaruing the passage of the X-ray beams generated from the X-ray target 22 and for absorbing the electron beams possibly generated within the tubular element 20. The thin film 24 may be omitted. Preferably, the thin film 24 may be a thin aluminum film of, say, about 2 μm in thickness thinner than the thickness of the thin film target 22 when the thin film target 22 is an aluminum layer. The thin film 24 may be selected from a beryllium layer, a carbon layer, or a high polymer layer coated with an aluminum layer or the like. Further, the thin film 24 is biased with a positive voltage supplied from a power source, so that the electrons generated in the capillary tubular element can be gathered and removed, efficiently.

A sufficiently converging electron beam 26 is applied to the thin film X-ray target 22. Preferably, the diameter of a suitable electron beam 26 is about 5 $\mu$m (the acceleration voltage is about 20 keV and the current is about 10 $\mu$A), which can be easily generated. The diameter of the electron beam 26 is controlled to be smaller than the diameter of the capillary tubular element 20. X-rays 28 are generated from the thin film X-ray target 22 and penetrate through the thin film.

The X-rays 28 are applied toward a specimen 25, so that the specimen 25 emits photoelectrons, which are detected by an electron spectrometer 29. The analyzer analyzes the energy of the photoelectrons. After being amplified, the energy of the photoelectrons is recorded in terms of the binding energy versus the intensitiy.

Figure 2:
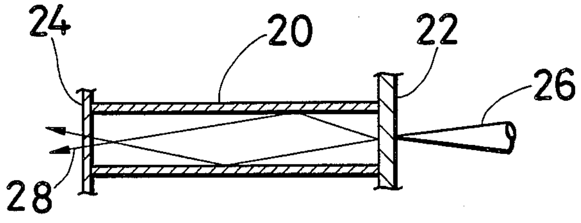
FIG. 2 is an enlarged cross-sectional view of a single capillary tubular element used for the X-ray source of FIG. 1.

FIG. 2 is an enlarged cross-sectional view of a single capillary tubular element 20 used for the X-ray source of FIG. 1. The electron beam 26 is incident on the X-ray target 22 of the single tubular element 20 to produce the X-rays 28 from the thin film 24.

Figure 3:
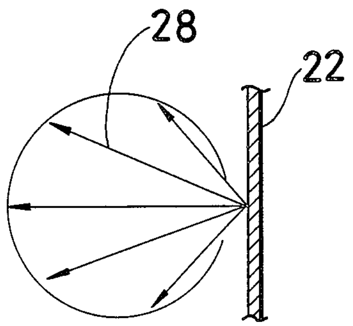
FIG. 3 shows a schematic distribution of the X-ray beams generated from a thin film X-ray target in the X-ray source of FIG. 1.
Figure 4:
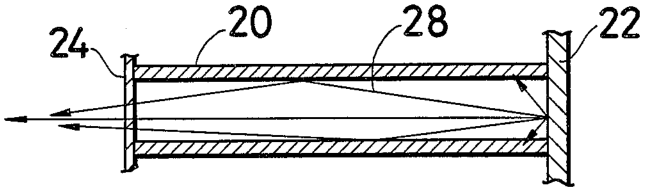
FIG. 4 is a cross-sectional view of the single capillary tubular element, showing the transmission of the X-ray beam in the capillary tubular element.
Figure 5:
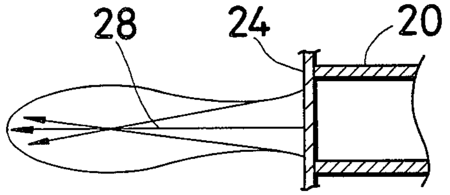
FIG. 5 is a cross-sectional view of the outlet of the single capillary tubular element, showing the emission of the X-ray beam from the outlet.
Figure 6:
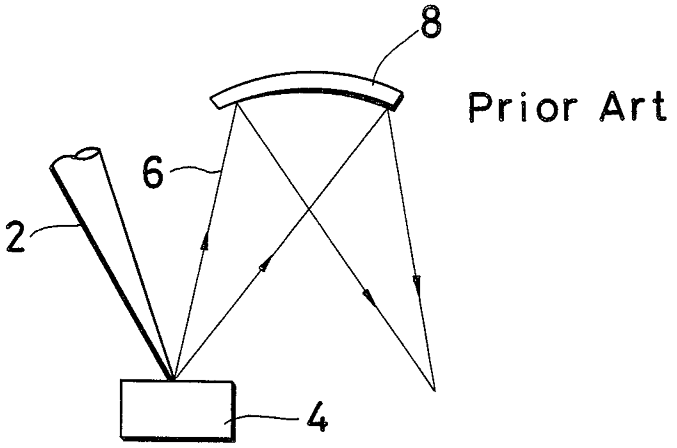
FIGS. 6 through 9 are cross-sectional views of a conventional X-ray source.
Figure 7:
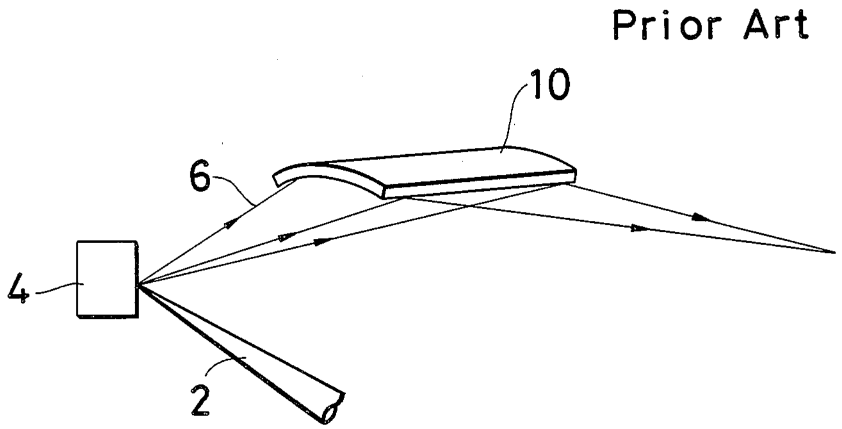
Figure 8:
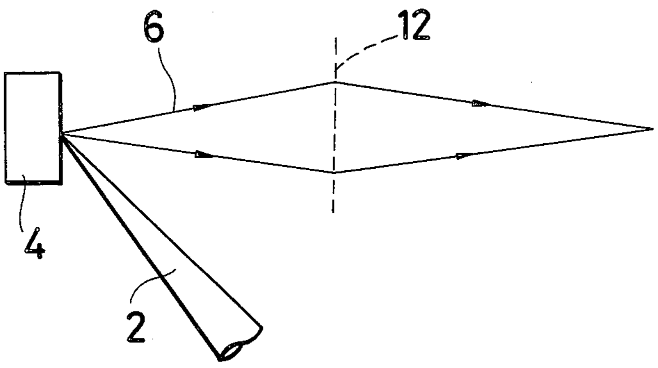
Fig. 8 Prior Art
Figure 9:
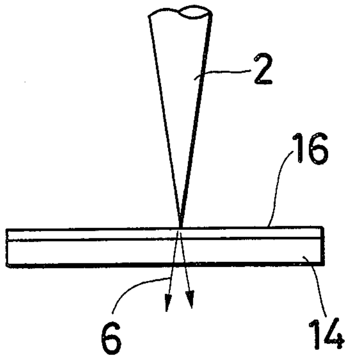
Fig. 9 Prior Art

The generation of the X-rays 28 will be described in detail. When the electron beam 26 becomes incident on the thin film X-ray target 22, the thin film X-ray target 22 generates characteristic X-rays (in this preferred embodiment, K$\alpha$ line of aluminum), which are propagated from both sides of the thin film X-ray target 22, e.g., into the inside and the outside of the capillary tubular element 20. With respect to the beams of the X-rays 28 emitting to the inside of the thin film X-ray target 22, the angle of directing the X-rays 28 is distributed as shown in FIG. 3. Among the beams of the X-rays 28 within the inside of the capillary tubular element 20, the beams of the X-rays 28 not impinging on the inner faces of the capillary tubular element 20 and the beams of the X-rays 28 totally reflected by the inner faces of the element 20 can emit to the outside through the thin film 24 with a small solid angle as shown in FIG. 4. Therefore, the beams of the X-rays 28 emitted through the thin film 24 are scattered with a distribution diameter similar to the diameter of the capillary tubular element 20. Owing to the total reflection of the capillary tubular element 20, the beams of the X-rays 28 can focus at a predetermined distance outside the outlet of the element 20 as shown in FIG. 5. The distance depends on the diameter and the length of the capillary tubular element 20, and the wavelength of the X-ray 28. Since the thin film 24 absorbs the electron beams generated from the inner side of the thin film X-ray target 22 and the inner surfaces of the capillary tubular element 20, those electron beams cannot emit to the outside through the thin film 24.

Thus, the scanning of the small electron beam 26 toward the thin film X-ray target 22 produces the X-ray beams 28. It may be possible that the diameter of the electron beam 26 impinging on the thin film X-ray target 22 can cover a plurality of capillary tubular elements 20 at the same time, whereby substantially parallel beams of the X-rays 28 with the large diameters can be generated from the thin film 24.

While only certain embodiments of the present invention have been described, it will be apparent to those skilled in the art that various changes and modifications may be made therein without departing from the spirit and scope of the invention as claimed.

What is claimed is:

1. An X-ray source for generating and focusing at least one X-ray beam at a small area of a specimen comprising:

at least one capillary tubular element having an entry end and an exit end;

an X-ray target positioned at the entry end of said at least one capillary tubular element for generating said at least one X-ray beam within said at least one capillary tubular element;

thin film means for absorbing extraneous electron beams generated within said at least one capillary tubular element as a result of generating said at least one X-ray beam, said thin film means being positioned at the exit end of said at least one capillary tubular element;

means for irradiating a converging electron beam source at said X-ray target for generating said at least one X-ray beam within said at least one capillary tubular element; and means, provided on the inner axial surface of said at least one capillary tubular element, for totally reflecting said at least one X-ray beam, wherein the at least one reflected X-ray beam is focused at a predetermined distance, exterior to said at least one capillary tubular element through said thin film means.

2. The X-ray source according to claim 1, wherein said X-ray target comprises an aluminum layer or a magnesium layer.

3. The X-ray source according to claim 1, wherein a power source means positively biases said thin film means.

4. The X-ray source according to claim 1, wherein said thin film means is thinner than said X-ray target.

5. An X-ray photoelectron spectroscopy system for generating an X-ray beam at a small area of a specimen comprising:

a plurality of capillary tubular elements grouped so as to have an entry end and an exit end;

an X-ray target positioned at the entry end of said plurality of capillary tubular elements;

thin film means for absorbing electron beams generating within said plurality of capillary tubular elements, said thin film means being positioned at the exit end of said plurality of capillary tubular elements;

means for irradiating converging electron beams at said X-ray target, wherein X-ray beams are generated along the axial interior length of said plurality of capillary tubular elements;

means, provided on the inner axial surface of each said plurality of capillary tubular elements, for totally reflecting the X-ray beams, wherein the reflected X-ray beams are focused at a predetermined distance exterior to said plurality of capillary tubular elements through said thin film means; and means for emitting photoelectrons from said specimen toward an X-ray photoelectron spectroscopy device as a result of said focused X-ray beam being applied to said specimen.

* * * * *